(12) United States Patent
Zhao

(10) Patent No.: US 8,207,192 B2
(45) Date of Patent: Jun. 26, 2012

(54) QUINUCLIDINE COMPOUNDS HAVING QUATERNARY AMMONIUM GROUP, ITS PREPARATION METHOD AND USE AS BLOCKING AGENTS OF ACETYLCHOLINE

(75) Inventor: Shuqiang Zhao, Beijing (CN)

(73) Assignee: Shuquiang Zhao, Beijing (CN)

( * ) Notice: Subject to any disclaimer, the term of this patent is extended or adjusted under 35 U.S.C. 154(b) by 539 days.

(21) Appl. No.: 12/400,053

(22) Filed: Mar. 9, 2009

(65) Prior Publication Data
US 2009/0163541 A1 Jun. 25, 2009

Related U.S. Application Data

(62) Division of application No. 11/575,384, filed as application No. PCT/CN2004/00104 on Sep. 15, 2004, now Pat. No. 7,521,559.

(51) Int. Cl.
A01N 43/90 (2006.01)
A61K 31/44 (2006.01)
C07D 453/02 (2006.01)
(52) U.S. Cl. ........................... 514/305; 546/137
(58) Field of Classification Search .............. 514/305; 546/137
See application file for complete search history.

(56) References Cited

OTHER PUBLICATIONS

Thacker et al., Drug safety: an international journal of medical toxicology and drug experience, (2006) vol. 29, No. 11, pp. 1077-1085.*
International Search Report for PCT/CN2004/001047 dated Aug. 18, 2005.
Journal of Medicinal Chemistry, 20 (10) p. 1250-1254, 1977.

* cited by examiner

*Primary Examiner* — Niloofar Rahmani
(74) *Attorney, Agent, or Firm* — Turocy & Watson, LLP

(57) ABSTRACT

The invention relates to the quinuclidine compounds of formula I having quaternary ammonium group, its preparation, and the pharmaceutical composition comprising an effective amount of the compound of formula I. The compound and the composition are used to prevent and treat the diseases by blocking acetylcholine receptor.

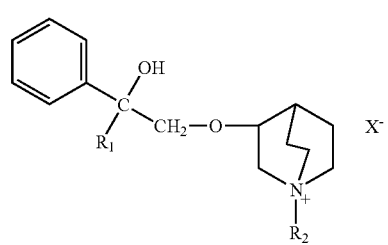

Wherein: $R_1$ is selected from $C_{1-12}$ saturated straight-chain alkyl and cycloalkyl; $R_2$ is selected from $C_{1-12}$ saturated straight-chain alkyl or straight-chain alkyl; and X is selected from halogen ion, organic and inorganic acid radical.

8 Claims, No Drawings

QUINUCLIDINE COMPOUNDS HAVING QUATERNARY AMMONIUM GROUP, ITS PREPARATION METHOD AND USE AS BLOCKING AGENTS OF ACETYLCHOLINE

CROSS REFERENCE TO RELATED APPLICATION

This application is a Divisional application of U.S. application Ser. No. 11/033,653, entitled USE OF TA-CAPPED METAL LINE TO IMPROVE FORMATION OF MEMORY ELEMENT FILMS and filed on Jan. 12, 2005, the entirety of which is incorporated herein by reference.

TECHNICAL FIELD

The present invention relates to an anticholinergic agent, especially to quinuclidine compounds having a quaternary ammonium group and preparation methods of the same, compositions comprising one or more such compound(s), and the use of the above compounds in preparation of anticholinergic agents.

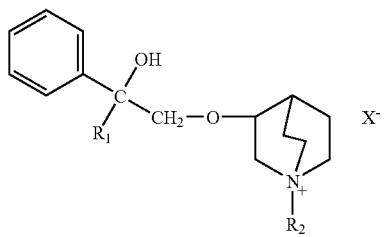

BACKGROUND OF THE INVENTION

Acetylcholine (ACh) is a kind of neurotransmitter released from the cholinergic nerve ending including motor nerve fiber, vegetative nerve preganglionic fiber, parasympathetic postganglionic fiber and part of sympathetic postganglionic fiber, which acts on cholinergic receptors, i.e., muscarine receptor (M-receptor) and nicotine receptor (N-receptor), with strong bioactivity. Cholinergic receptor blocking agents, which can be divided into M-choline receptor blocking agents and N-choline receptor blocking agents, act to block the choline receptor. M-choline receptor blocking agents can block the choline receptors on the effectors dominated by the central and the postganglionic cholinergic nerve, which exhibits pseudo-mentation of the central nerve, chalasia of the smooth muscles, inhibition of glandular secretion, mydriasis, speeded cardiac rhythm and the like, and thus, they have extensive pharmacological functions and clinical uses.

At present, nearly all of M-choline receptor blocking agents are tropine-base alkaloids or artificial atropine substitutes. Due to their extensive pharmacological effects, when they are used for a certain effect, other effects become side effects, especially the psychomimetic effect. This limits their clinical uses and thus, the anticholinergic agents should have selectivity, i.e., maintaining their anticholinergic effect while reducing the adverse effect of the center nerve psychomimetic effect.

Up to this date, there is no report about the quinuclidine compounds having a quaternary ammonium group as disclosed in the present invention, nor is there any report about the use thereof in blocking cholinergic receptor as an anticholinergic agent.

SUMMARY OF THE INVENTION

To overcome the defects of the prior medicaments and techniques, one aspect of the present invention is to provide a novel quinuclidine compound having quaternary ammonium group.

Another aspect of the present invention is to provide a method of preparing the quinuclidine compound having quaternary ammonium group.

A further aspect of the present invention is to provide one or more pharmaceutical composition(s) comprising the above compound and pharmaceutically acceptable carriers, such as tablets, capsules, aerosols, sprayers, injections or slow-release formulations.

Yet another aspect of the present invention is to provide a use of the above compound in preparing anticholinergic agents.

For the aspects of the present invention, the following technical solutions are provided:

The present invention relates to a novel compound of Formula I:

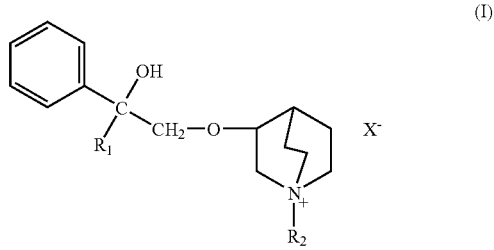

wherein,
$R_1$ is selected from saturated straight-chain alkyl and cycloalkyl containing 1 to 12 carbon atoms,
$R_2$ is selected from saturated straight-chain alkyl or straight-chain alkyl containing 1 to 12 carbon atoms, and
X is selected from halide ion, pharmaceutically acceptable acid radicals such as organic and inorganic acid radicals.

The method of preparing the compound of Formula I of the present invention comprises reacting phenylalkylethylene oxide and 2-quinuclidinol with strong base in an organic solvent, then isolating the diastereoisomer by chromatography, and finally reacting with halogenated alkane.

Specifically, the method of preparing the compound of Formula I comprises the following acts:

(A) reacting phenylalkylethylene oxide and 2-quinuclidinol with strong base in DMSO;

(B) reacting the product of act (A) with halogenated alkane to prepare racemic compound containing quaternary ammonium group;

(C) isolating the product of act (A) by chromatography to prepare a pair of diastereomeric compounds and corresponding pure optical isomer compounds.

(D) reacting the products of act (C) with halogenated alkane, respectively, to prepare stereoisomeric compounds containing quaternary ammonium group.

The present invention also relates to a pharmaceutical composition comprising an effective amount of the compound of Formula I and pharmaceutically acceptable carriers.

According to the pharmacological study, the compound of Formula I of the present invention has an activity of blocking cholinergic receptor, and the compound of the present invention exhibits a notable inhibition to specific allergic asthma of guinea pigs. More importantly, the compound of the present invention cannot penetrate through the blood-brain barrier or enter into the central nerve system, and thus, it does not present an adverse effect of the center nerve psychomimetic effect.

The compounds of the present invention are cholinergic receptor blocking agents that cannot enter into the central nerve system, and they can be used in treatment of bronchial asthma, chronic obstructive pulmonary disease, common cold, rhinitis, peptic ulcer, diarrhea, arrhythmia, etc.

The pharmaceutical composition comprising an effective amount of the compound of the present invention can be prepared by using common carriers known in the art.

The compound of the present invention or the composition thereof can be administered via oral or parenteral methods. The oral formulations include tablet, capsule, coating, pulvis, and oral liquid. The parenteral formulations include aerosol, sprayer, drop, injection, and suppository. These formulations are prepared by common methods known to the skilled in the art. The dressings for the preparation of tablet, capsule, coating, pulvis, are common assistants, including, for example, starch, dextrin, microcrystalline cellulose, pregelatinized starch, gelatin, acacia gum, methyl cellulose, ethyl cellulose, hydroxypropyl cellulose, sodium carboxymethyl cellulose, silica, and polyethylene glycol. The solvents for liquid formulations are water, ethanol, propylene glycol, vegetable oils such as corn oil, arachis oil, and olive oil, etc. The formulations of the compounds of the present invention can also contain other assistants, such as surfactant, lubricant, disintegrant, preservative, odor-masking agent and colorant.

The dosage of the compound of Formula I of the present invention contained in tablet, capsule, coating, aerosol, sprayer, injection and suppository is calculated based on the amount of the compound presented in unit formulation. The unit formulation generally contains 1-5000 μg of the compound of Formula I of the present invention.

For the treatment of bronchial asthma, chronic obstructive pulmonary disease, common cold, rhinitis, and the like, an adult patient could be administered with the compound of the present invention by spray, once or separately, with a dosage of 1-1000 μg, preferably 1-100 μg per day.

PREFERRED EMBODIMENTS OF THE INVENTION

The present invention is further described by the following examples. However, these examples cannot be taken as the limitation of the present application. The measurement instruments used herein are listed below: melting-point is measured by XRC-1 micromelting point apparatus without calibration of thermometer; NMR spectroscopy is measured by Bruker ARX500 nuclear magnetic resonance analyzer with TMS as the internal standard; the mass spectrum is determined by Nicoler FTMS-2000G apparatus.

Example 1

The preparation of 3-quinuclidinyl-(2'-phenyl-2'-cyclopentyl-2'-hydroxyl)ethyl Ether (1)

9.3 g 1-phenyl-1-cyclopentyl ethylene oxide was dissolved in DMSO. To 64 ml of DMSO was dissolved 6.35 g quinuclidinol, then 2.5 g sodium hydride was added. After stirring for 1 hour, the solution was cooled to room temperature. Then dropped with a solution of 1-phenyl-1-cyclopentyl ethylene oxide in DMSO, and stirred for additional 3 hours. After cooling to room temperature, the solution was extracted with ether, and the ether layer was extracted with 6N HCl. The acid aqueous layer was then basified by 20% NaOH, and then extracted with ether. The ether layer was dried over anhydrous sodium sulfate overnight, the solvent was evaporated, and the product was purified through distillation with a yield of 54%.

Example 2

The preparation of 3-(N-methyl-quinuclidinyl)-(2'-phenyl-2'-cyclopentyl-2'-hydroxyl)ethyl Ether Bromide (2)

The compound (1) obtained in Example 1 was dissolved in anhydrous ethanol, and then aerated with excess bromomethane, and reacted overnight. After evaporation of the solvent, the product was recrystallized with acetone to give a white solid with a yield of 75%. The melting point is 166-168° C.; $^1$HNMR (CDCl$_3$): 7.42 (d, 2H), 7.29 (g, 2H), 7.20 (t, 1H), 4.29 (m, 1H), 3.96 (br, 1H), 3.85 (m, 1H), 3.70 (m, 4H), 3.30 (d, 1H), 3.22 (s, 3H), 3.11 (m, 2H), 2.25 (m, 2H), 1.96 (m, 2H), 1.63 (m, 4H), 1.44 (m, 4H), 1.26 (m, 2H). MS (m/z): 410 (M$^+$); 175, 726 (B).

Example 3

The Preparation of I-Type Diastereoisomer of 3-(N-methyl-quinuclidinyl)-(2'-phenyl-2'-cyclopentyl-2'-hydroxyl)ethyl Ether Bromide (3)

Compound (1) was isolated by preparative silica gel plate with CHCl$_3$:methanol:ammonia (4:0.8:0.15) as the developer. After collecting the chromatographic band with high R$_f$ value, the eluted product was aerated with excess bromomethane, and reacted overnight. After evaporation of the solvent, the product was recrystallized with acetone to give a white solid with a yield of 30%. The melting point is 149-151° C.

Example 4

The Preparation of II-Type Diastereoisomer of 3-(N-methyl-quinuclidinyl)-(2'-phenyl-2'-cyclopentyl-2'-hydroxyl)ethyl Ether Bromide (4)

Compound (1) was isolated by preparative silica gel plate with CHCl$_3$:methanol:ammonia (4:0.8:0.15) as the developer. After collecting the chromatographic band with low R$_f$ value, the eluted product was aerated with excess bromomethane, and reacted overnight. After evaporation of the solvent, the product was recrystallized with acetone to give a white solid with a yield of 30%. The melting point is 160-162° C.

Example 5

In Vitro Anti-Acetylcholine Effect of the Compound of the Present Invention

This experiment adopts the methods known to the skilled in the art. An ex vivo ileum specimen was prepared and suspended in a 30 ml bath filled with Tyrode's solution. The nutrient fluid was aerated with a mixed gas of 95% O$_2$ and 5%

$CO_2$, and maintained a constant temperature of 37° C., then an irritating electrode was equipped. Irritation was performed with a square wave with a frequency of 0.1 times/s and duration of 1 millisecond. The ileum will take place a transient contraction upon one irritation. Before changed to other Tyrode's solution containing different medicament, it is necessary to wash with the Tyrode's solution for three times and carry out a blank irritation. Consequently, the ileum contraction response resulted from electric irritation is completely blocked in Tyrode's solutions containing $10^{-7}$ g/ml of atropine sulfate, the compounds of Example 2, Example 3 and Example 4, respectively.

The preparation of the aerosol containing the compound of the present invention:

Example 6

0.28 g of the compound of the present invention, 35 g propylene glycol, 382 g ethanol and 983 g propellant are sealed into containers with proportional valves. Each container has 10 g of the above mixture, and each spray is 100 mg with 20 μg of the compound of the present invention. The propellants are selected from the group consisting of trichloromonofluoromethane, dichlorodifluoromethane, dichloromonofluoromethane, monochlorodifluoromethane, dichlorotetrafluoroethane, chloropentafluoroethane, chlorodifluoroethane, difluoroethane, octafluorocyclobutane and the mixture thereof.

Example 7

0.28 g of the compound of the present invention, 42 g propylene glycol, 210 g anhydrous ethanol, 231 g dichlorodifluoromethane and 971 g dichlorotetrafluoroethane are sealed into containers with proportional valves. Each container has 10 g of the above mixture, and each spray is 100 mg with 20 μg of the compound of the present invention.

Example 8

The Effect of the Aerosol Containing the Compound of the Present Invention in Treatment of the Specific Allergic Asthma of Guinea Pigs This experiment adopts the methods known to the skilled in the art. 30 healthy guinea pigs with body weights of 200-220 g are picked in the experiment. Each guinea pig is intraperitoneally injected with 1.0 ml 10% ovalbumin physiological saline solution (100 mg of ovalbumin). Thereafter, they are randomly separated into blank control group, positive control group [Atrovent (IpratropiumBromide aerosol), 10 ml per container, 20 μg per spray, made by Boehringer Ingelheim of Germany, Batch No. 104015, manufacture date: June, 2001, term of validity: June 2004], aerosol group of the compound of Example 2, aerosol group of the compound of Example 3, and aerosol group of the compound of Example 4, with ten guinea pigs each group. The guinea pigs are administrated by spraying into the respiratory tract once a day for 5 days continuously from the $6^{th}$ day after the injection. Then they are put into sealed cages separately and 0.5% ovalbumin physiological saline solution was sprayed evenly into the cages by ultrasonic atomizer for 30 s. The time interval between the spray of the ovalbumin physiological saline solution and the contraction of the abdominal muscle, also known as the asthma latent period, is observed and recorded. The obtained data are t-tested to demonstrate the differences among the groups.

Results: 10 days after the guinea pigs were intraperitoneally injected with ovalbumin, when they contacted with the same antigen again, the antigen-antibody reaction that mainly involves dropsy and spasm of the respiratory tract occurs, which is called specific allergic asthma. The experiment demonstrates that the aerosol of the present compound exhibits notably inhibition to this specific reaction, in which the asthma latent period is obviously prolonged as compared to that of the blank control group, P<0.01. The results are listed in Table 1 below.

TABLE 1

The effect of the aerosol containing the compound of the present invention on allergic asthma of guinea pigs (s $\overline{X}$ ± SD)

| Group | n | Dosage (μg · kg$^{-1}$) | latent period (s) |
|---|---|---|---|
| Blank control | 10 | — | 124.00 ± 21.66 |
| Positive control | 10 | 100 | 235.40 ± 45.15** |
| aerosol of the compound of Example 2 | 10 | 100 | 248.90 ± 38.24** |
| aerosol of the compound of Example 3 | 10 | 100 | 243.50 ± 42.13** |
| aerosol of the compound of Example 4 | 10 | 100 | 231.60 ± 37.30** |

Compared with the blank control group **P < 0.01

INDUSTRIAL APPLICABILITY

According to the above experimental results, those skilled in the art will understand that the compounds of the present invention can block the mammalian M-choline receptor. In addition, the compounds of the present invention have a promising prospect in preparing M-choline receptor blocking agents for mammals, including human.

What is claimed is:

1. A method of blocking cholinergic receptors comprising administering to a patient a compound having quaternary ammonium group of Formula I:

(I)

wherein, $R_1$ is selected from saturated straight-chain alkyl and cycloalkyl containing 1 to 12 carbon atoms, $R_2$ is selected from saturated straight-chain alkyl and straight-chain alkyl containing 1 to 12 carbon atoms, and X is selected from halide ion, organic and inorganic acid radicals.

2. The method of claim 1, wherein $R_1$ is cyclopropyl, cyclopentyl or cyclohexyl; $R_2$ is methyl, ethyl, propyl, isopropyl, n-butyl, isobutyl or t-Butyl; X is fluorine, chlorine, bromine, iodine, methanesulfonic acid radical, paratoluenesulfonic acid radical, or other pharmaceutically acceptable acid radicals.

3. The method of claim 1, wherein $R_1$ represents cyclopentyl; $R_2$ represents methyl; X represents bromine.

4. The method of claim 1, wherein a configuration of the compound is diastereoisomer.

5. The method of claim 1, wherein a configuration of the compound is pure optical isomer.

6. A method of treating specific allergic asthma comprising administering to a patient a compound having quaternary ammonium group of Formula I:

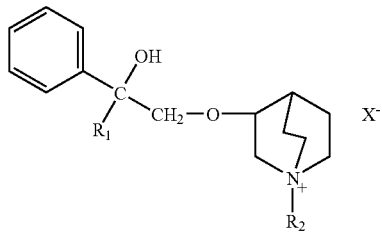

(I)

wherein, $R_1$ is selected from saturated straight-chain allyl and cycloalkyl containing 1 to 12 carbon atoms, $R_2$ is selected from saturated straight-chain alkyl and straight-chain alkyl containing 1 to 12 carbon atoms, and X is selected from halide ion, organic and inorganic acid radicals.

7. The method of claim 6, wherein $R_1$ is cyclopropyl, cyclopentyl or cyclohexyl; $R_2$ is methyl, ethyl, propyl, isopropyl, n-butyl, isobutyl or t-Butyl; X is fluorine, chlorine, bromine, iodine, methanesulfonic acid radical, paratoluenesulfonic acid radical, or other pharmaceutically acceptable acid radicals.

8. The method of claim 6, wherein $R_1$ represents cyclopentyl; $R_2$ represents methyl; X represents bromine.

* * * * *